United States Patent [19]

Akyu

[11] Patent Number: 5,725,152
[45] Date of Patent: Mar. 10, 1998

[54] AIR FRESHENER DISPENSER

[75] Inventor: Muneki Akyu, Nara, Japan

[73] Assignee: Okamoto Industry Co., Ltd., Nara, Japan

[21] Appl. No.: 622,123

[22] Filed: Mar. 26, 1996

[30] Foreign Application Priority Data

Oct. 25, 1995 [JP] Japan .................... 7-277815

[51] Int. Cl.$^6$ ...................................... A61L 9/04
[52] U.S. Cl. ................ 239/45; 239/47; 239/51.5; D23/366
[58] Field of Search .................. 239/34, 42–47, 239/51.5, 53–57, 145, 289, 326; D23/366–369

[56] References Cited

U.S. PATENT DOCUMENTS

| | | | |
|---|---|---|---|
| 1,644,482 | 10/1927 | Muller | 239/47 |
| 1,886,429 | 11/1932 | Saeks | 239/53 |
| 1,989,883 | 2/1935 | Redwine | 239/44 |
| 2,492,039 | 12/1949 | Gilowitz | 239/44 |
| 2,507,899 | 5/1950 | Gilowitz | 239/44 |
| 2,631,890 | 3/1953 | Fink | 239/34 |
| 4,165,835 | 8/1979 | Dearling | 239/51 |
| 4,293,095 | 10/1981 | Hamilton et al. | 239/47 |
| 4,708,851 | 11/1987 | Von Loringhoven | 239/56 |
| 4,732,321 | 3/1988 | Dolan | 239/45 |
| 4,739,928 | 4/1988 | O'Neil | 239/45 |
| 4,919,981 | 4/1990 | Levey et al. | 239/44 |
| 4,928,881 | 5/1990 | Barlics et al. | 239/44 |
| 5,000,383 | 3/1991 | Van Der Heijden | 239/47 |
| 5,014,913 | 5/1991 | Hoyt et al. | 239/45 |
| 5,077,102 | 12/1991 | Chong | 239/47 |

*Primary Examiner*—Andres Kashnikow
*Assistant Examiner*—Lisa Ann Douglas
*Attorney, Agent, or Firm*—Price, Gess & Ubell

[57] ABSTRACT

An air freshener dispenser is provided with an emanator medium which is easily replaced, allowing for sustainable use of the container. The dispenser is characterized by having a head section consisting of a head assembly and a fixing member. The head assembly is detachably connected to the container, comprising a cylindrical cap member having a plurality of threads for mating with threads on the outer periphery of the container neck and an exterior ornamental part extending upwardly and outspreadly from the outermost periphery of the cap member. The fixing member is inserted into the space surrounded by the thread in such a way that the emanator medium is firmly held therebetween, its base being in tight contact with the wick which carries the fragrant liquid thereto by capillary action.

13 Claims, 6 Drawing Sheets

AIR FRESHENER DISPENSER

BACKGROUND OF THE INVENTION

1. Field of the Invention

The present invention relates to an air freshener dispenser which is used for deodorization and fragrancing a room, a car, or the like by volatilizing a fragrant liquid.

2. Description of Relevant Art

An ordinary air freshener dispenser as shown in FIG. 7 employs a reservoir 120 for containing a liquid fragrance composition therein having a wick 121 which carries the liquid to an odor-emitting paper 112 by capillary action. The paper 112 is in tight contact with the top of the wick 121, so that the paper absorbs the fragrant liquid which is then volatilized therefrom to the atmosphere.

Since the odor-emitting paper 112 is normally not designed to be replaced, it is usually fixtured within an annular supporter 111 of a paper holder 110, and thus it cannot be readily removed or replaced. Moreover, a cover member 100 in such type of dispenser is usually made of plastic and formed by unitary molding and is often further coated with a facing cover with ornamental patterns to improve the appearance and to enhance the commercial value.

Generally, the odor-emitting paper becomes clogged up with solid fragrant substances in the liquid as time passes, which lowers the efficiency of volatility. At the same time the paper discolors unpleasantly by the accumulation of non-volatile substances, which may damage the whole appearance of the container in case that the paper is visible from outside. Since the above-described conventional air freshener dispenser does not allow for replacement of the odor-emitting paper 112, the whole dispenser including the container 120, the paper holder 110, the cover member 100, and the other elements must be wastefully discarded when it can be no longer used because of the deterioration of volatility due to the clogged paper. For the same reason, there are few who use the dispenser for a long time by refilling the fragrant liquid, which causes waste of resources. Furthermore, the above-described type of dispenser demands a cover member 100 other than a container 120 and a paper holder 110, which further requires ornaments thereon for aesthetic reasons, and thus the cost of production is relatively high.

SUMMARY OF THE INVENTION

In view of the foregoing, it is a primary object of the present invention to provide an air freshener dispenser, an emanator medium of which can be readily replaced so that the whole dispenser can be used for a long time even if the emanator medium becomes clogged or unpleasantly discolors.

Another object of this invention is to reduce the cost and increase the productivity as well as to improve the appearance of the dispenser without any specific ornamental elements by forming a head section in the shape of a flower.

The above-described objects are accomplished by providing an air freshener dispenser comprising a container having a neck with an opening for containing a volatile fragrant liquid, a head section removably connected to the top of the container, an emanator medium made of an absorbent material detachably retained in the head section, and a wick for providing the emanator medium with the fragrant liquid. The head section consists of a head assembly and a fixing member. The head assembly comprises a hollow cylindrical cap member suitable for mating with the container neck, an exterior ornamental part extending upwardly from the outermost periphery of the cap member, and a retaining portion having a plurality of grippers extending uprightly from the top of the cap member and surrounding an opening of the cap member therein. The emanator medium is bent at approximately right angle along lines between a plurality of standing parts and a bottom part. The fixing member is inserted into the retaining part of the head assembly in such a way that the emanator medium is held between its outer periphery and the grippers, bringing the emanator medium in tight contact with the top of the wick.

According to the present invention, the head section is connected to the neck of the container having the impregnated wick therein. The top end of the wick extends through both openings of the container and the cap member of the head assembly and is brought into tight contact with the emanator medium which is secured in the head section by the fixing member and the grippers of the head assembly. The fragrant liquid is transported through the wick by capillary action and is supplied to the emanator medium, from where it is volatilized to the atmosphere. Replacement of the emanator medium only requires detaching the fixing member from the head assembly, as the fixing member can be readily extracted from the head section due to the resiliency of the grippers, thereby releasing the emanator medium from the retained state. While the emanator medium needs to be bent to make the standing parts when used, it can be stored in a flat state, thereby saving store space.

A wick holder inside the container neck may be preferably provided with vent holes. A plurality of small bosses may also be further provided on the annular top surface of the cap member so that there is a gap between the bottom part of the emanator medium and the top surface of the cap member. The vent holes and the gap permit air to flow between interior and exterior of the container, whereby assuring a safe use of the dispenser by obviating an ejection of the fragrant liquid which may be caused by high inner pressure when used under a high temperature.

It is also an advantage of the present invention to have an eye-pleasing appearance without any special elements for decoration only by forming the exterior ornamental part, the emanator medium, and the fixing member in the shape of a petal, a stamen, and a pistil, respectively. The whole container consisting of only essential elements thus looks like an artificial flower, contributing to low cost and high productivity compared to a conventional type of air freshener dispenser having a cover member with facing ornaments.

DESCRIPTION OF THE PREFERRED EMBODIMENTS

Figure 1:
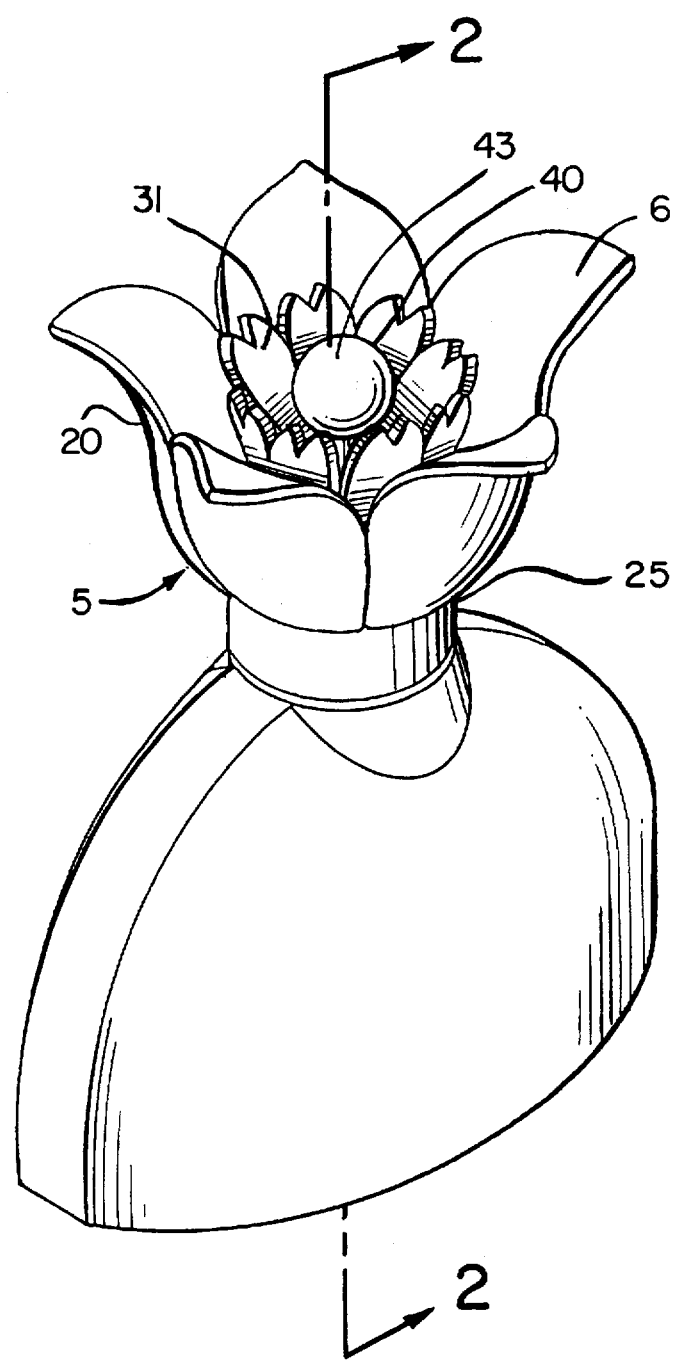
FIG. 1 is a perspective view showing a first embodiment of the present invention.
Figure 2:
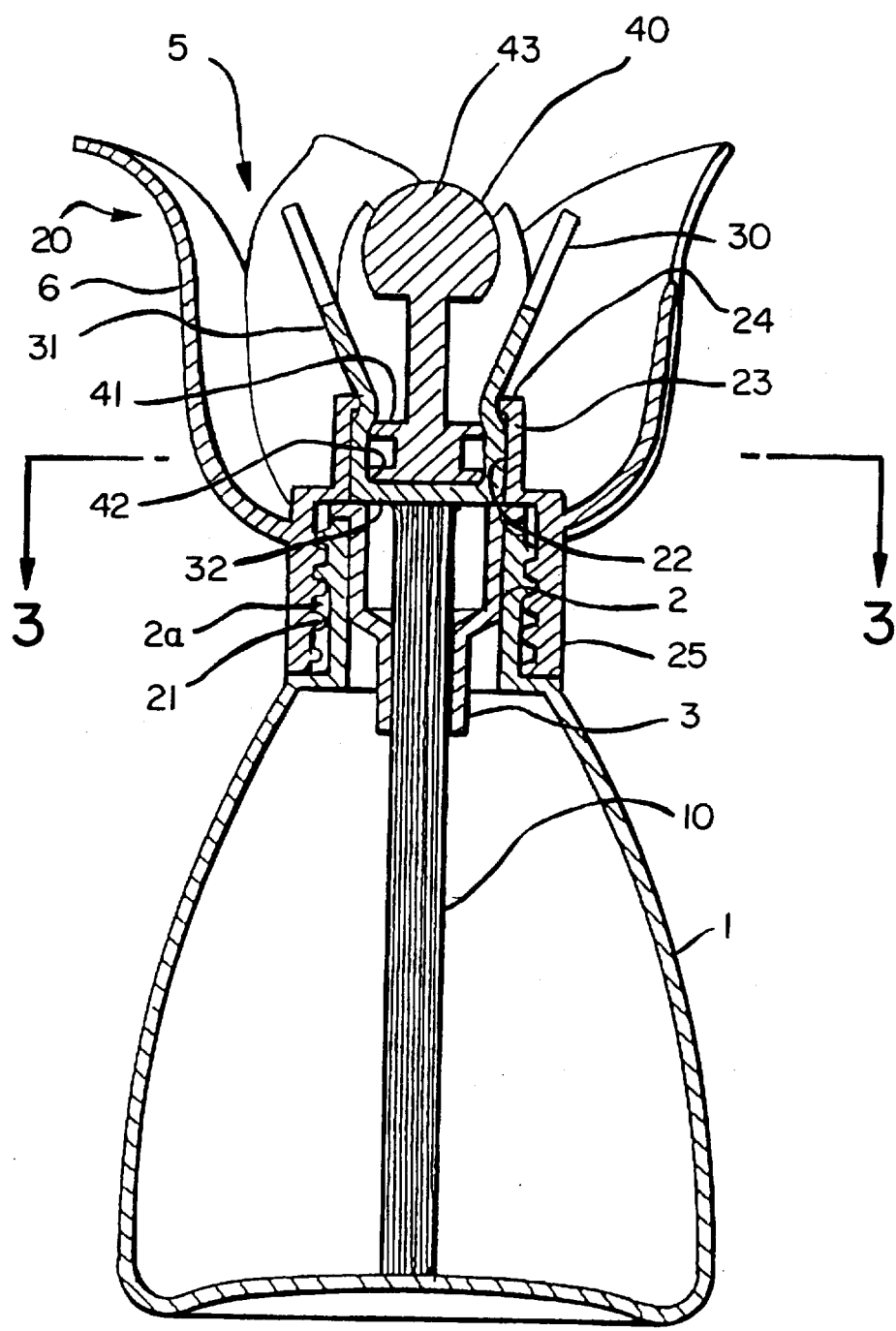
FIG. 2 is a vertical cross-sectional view thereof.
Figure 3:
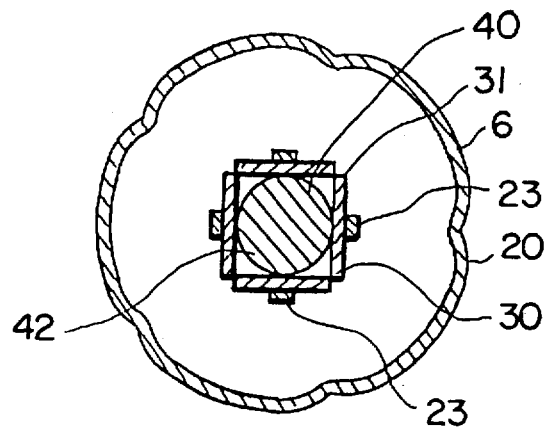
FIG. 3 is a sectional view across lines A—A of FIG. 2.

Referring to the drawings 1 and 2, a container 1 with an opening made of plastic generally having an elliptical base and a neck 2 provided with outer peripheral threads 2a. Depending from the opening of the neck 2 downwardly into the interior of the container 1 is a wick 10 held by a wick holder 3, a top end of which extends slightly above the annular top surface of the neck 2. The wick 10 is preferably made of an absorbent fiber such as polyester which may be interwined or braided into a wick.

A head section 5 is detachably connected to the container neck 2. The head section 5 consists of a head assembly 20 and a fixing member 40. The head assembly 20 comprises a cap member 25 being a hollow cylindrical shaft and provided with threads 21 on its inner wall suitable for mating with the threads 2a on the outer periphery of the container neck 2. Depending from the outermost periphery of the cap member 25 is an ornamental skirt 6, extending upwardly and outspreadly in a manner that it looks like a flower petal. Interior of the skirt 6 at the bottom opens an opening 22 of the cap member 25, and the wick 10 extends slightly above the rim of the opening 22 when the head assembly 20 is rotatably secured to the container neck 2 by means of the complementary threads 21 and 2a on the cap member 25 and on the container neck 2, respectively. On the annular top surface of the cap member 25 extend four grippers 23 uprightly disposed at equal distance surrounding the opening 22. Each gripper 23 has a hook 24 at its top end and sufficient flexibility so that it can be bent outwardly. The whole head assembly 20 is made of plastic and formed by unitary molding.

Figure 4:
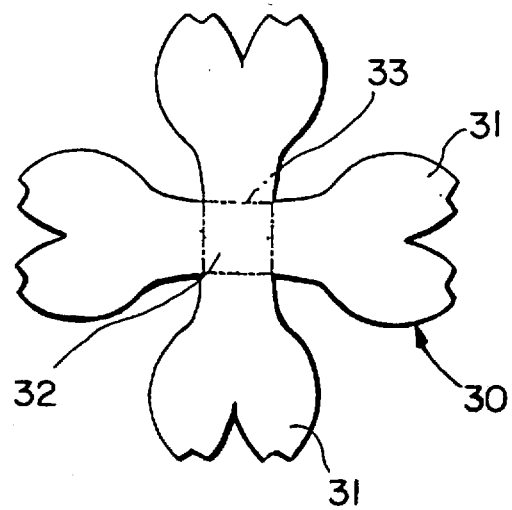
FIG. 4 is a top plan view of an emanator medium of the present invention during nonuse.
Figure 5:
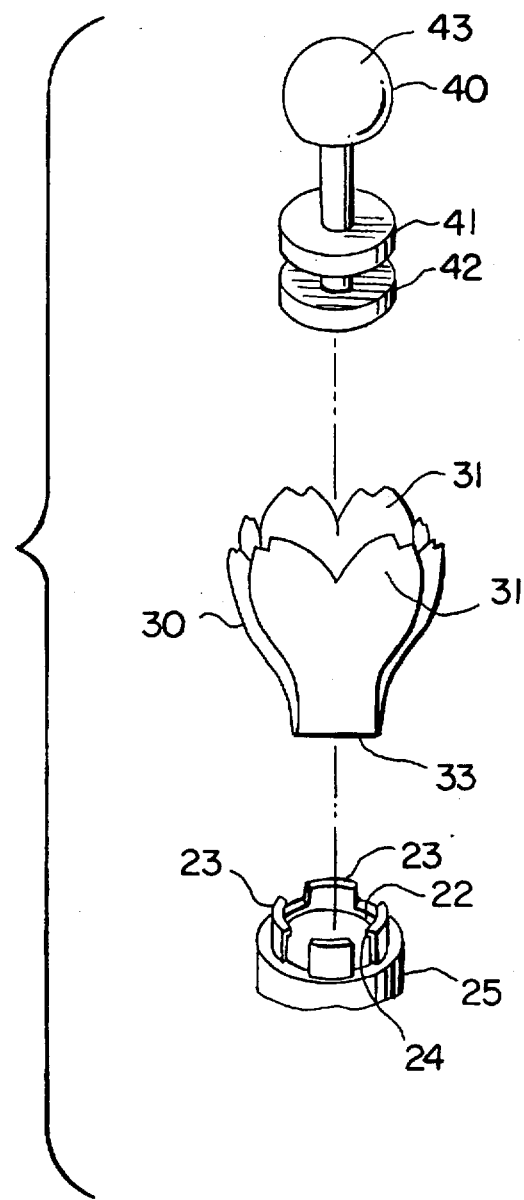
FIG. 5 is an exploded perspective view of an emanator medium of the present invention when secured in a head assembly of the same.

Referring to the drawings 3, 4, and 5, an emanator medium 30 is made of an absorbent material such as filter paper or felt and generally cut in the form of a cross of appropriate width. Outer four sides of the emanator medium 30 make standing parts 31, each having a fringed edge in a way that it imitates a figure of a stamen when the emanator medium 30 is secured in the head assembly 20. The central square part of the emanator medium is a bottom part 32. Between the standing parts 31 and the bottom part 32 are creases 33 shown by dot-dash lines in FIG. 4, in which four standing parts 31 are bent upwardly at an approximately right angle when used.

The fixing member 40 is of plastic material and comprises a slim rod having a round top 43 and an upper annular peripheral flange 41 and a lower annular flange 42 disposed vertically at regular distance with respect to each other. The fixing member 40 is formed as described above so as to imitate a figure of a pistil when it is set in the head assembly 20. The diameter of the flanges 41, 42 is slightly greater than the deduction of the thickness of the emanator medium 30 from the bore of the opening 22, so that the emanator medium 30 is retained between the fixing member 40 and the grippers 23. When the fixing member 40 is inserted into the inner space surrounded by the grippers 23, the emanator medium 30 having a proper thickness is tightly held therebetween, a part of which being pushed into the intervals of the flanges 41, 42 and securely caught by the hooks 24 of the grippers 23. The hooks 24 catching the upper flange 41 also assures a stable support of the fixing member 40. The bottom part 32 of the emanator medium 30 is firmly pressed onto the top end of the wick 10 by the lower flange 42 of the fixing member 40 for receiving the liquid fragrance.

By assembling a plurality of above described elements, the dispenser of the present invention gains an artificial flower-like appearance. The same dispenser can be continuingly employed for a long time by refilling the fragrant liquid, and even if the emanator medium 30 becomes clogged up with solid fragrant substances, it can be readily replaced by only releasing the fixing member 40.

Figure 6:
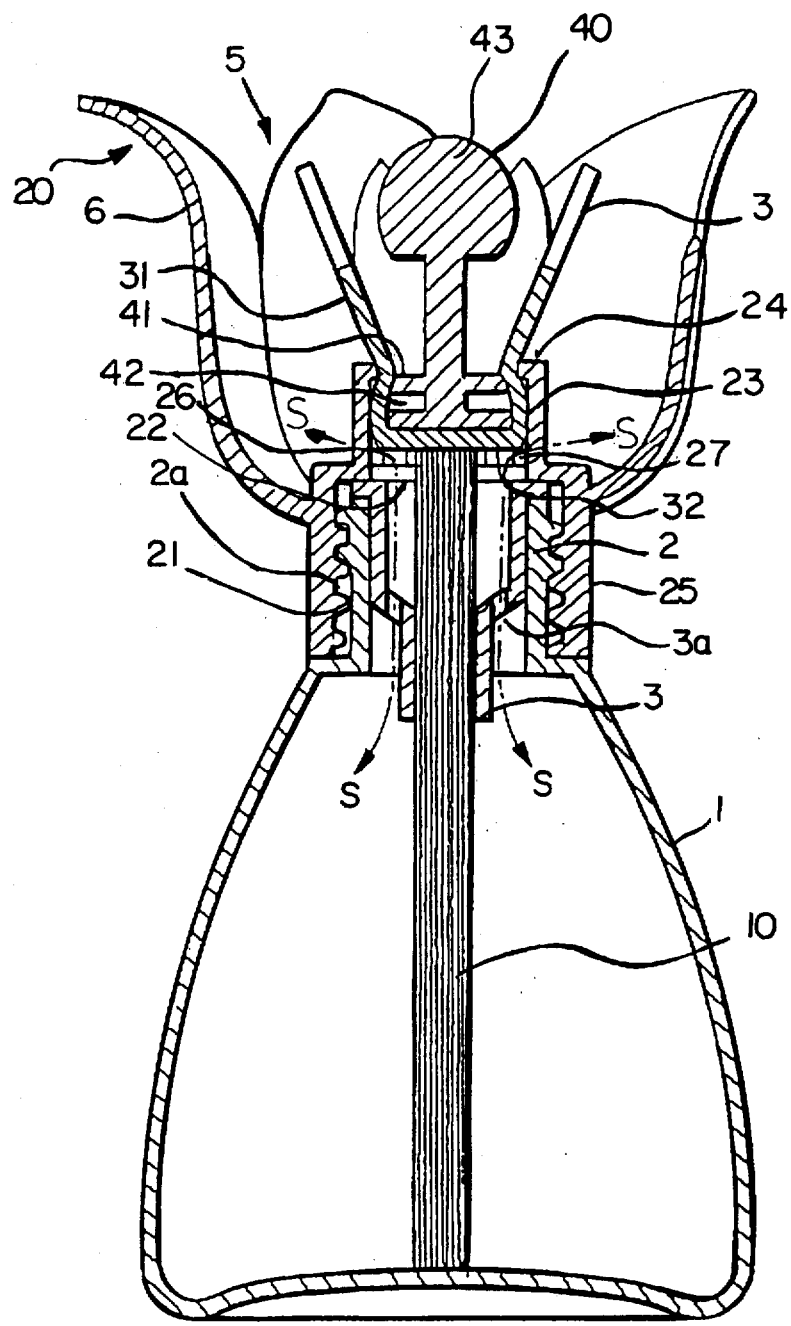
FIG. 6 is a vertical cross-sectional view of a second embodiment of the present invention.
Figure 7:
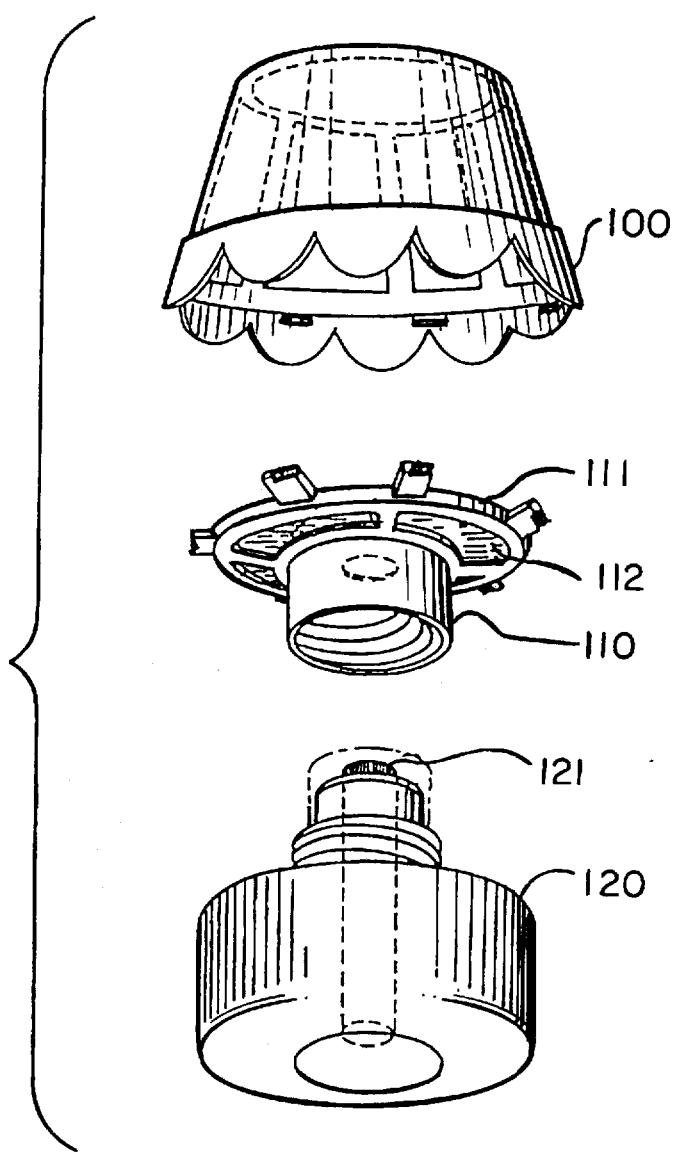
FIG. 7 is an exploded perspective view of a conventional air freshener dispenser.

FIG. 6 shows a second embodiment of the present invention, wherein a plurality of bosses 26 are provided on the annular top surface of the cap member 25 between the grippers 23, 23 in such a way that there is a gap 27 between the bottom part 32 of the emanator medium 30 and the top of the cap member 25. The wick holder 3 supporting the wick 10 is provided with vent holes 3a in its outer circumferential part. The gap 27 and the vent holes 3a make a path for airflow designated as S in FIG. 6 between interior and exterior of the container 1, which prevents inner space of the container 1 from being highly pressurized when used under a high temperature, whereby it obviates an ejection of the fragrant liquid and assures a safe use of the dispenser.

It should be also understood that forgoing relates to only a preferred embodiment of the invention, ant that it is intended to cover all changes and modifications of the example of the invention herein chosen for the purposes of the disclosure, which do not constitute departures from the spirit and scope of the invention.

We claim:

1. An air freshener dispenser comprising:

a container having a neck with an opening for containing a fragrant liquid composition;

a wick depending downwardly into the container supported by a wick holder;

a head assembly monolithically molded including a hollow cylindrical member suitable for mating the head assembly with the neck of the container, an exterior ornamental part extending upwardly and outspreadly from the outermost of the cylindrical member, a plurality of retaining means formed on the top of the cylindrical member to extend uprightly therefrom and disposed circumferentially at a predetermined interval to surround an opening matching with the container opening;

an emanator medium of an absorbent material removably retained in the head assembly, having a bottom part and ambient parts; and a fixing member substantially comprising a shaft and a flat bottom, vertically inserted into an inner space defined by the retaining means of the head assembly for connecting the emanator medium to the head assembly, thereby holding the bottom part of the emanator medium in fluid contact with the top of the wick as well as causing the ambient parts of the emanator medium to stand upright.

2. The air freshener of claim 1, where the wick holder is provided with a plurality of vent holes, and the top surface of the cylindrical member is provided with a plurality of upward protrusions to make a gap between the bottom part of the emanator medium and the top surface of the cylindrical member, whereby allowing air to flow between interior and exterior of the container.

3. The air freshener dispenser of claim 1, wherein the exterior ornamental part of the head assembly is formed in the shape of a petal, the emanator medium in the shape of a stamen, and the fixing member in the shape of a pistil, respectively.

4. An air freshener dispenser comprising:

a container having an opening and storing a fragrant evaporable liquid;

a head assembly connected to the container adjacent the opening and simulating petals of a flower comprising a plurality of flexible cantilevered gripper members;

an absorbent material removably connected to the head assembly and operatively connected to the opening, the absorbent material extending upward from the container and configured to complement the simulated petals of the head assembly;

delivery means extending from the opening into the container to deliver the fragrant evaporable liquid to the absorbent material; and a fixing member removably connected to the head assembly, mounted between the gripper members and extending the absorbent material upward from the opening and the gripper members, and securing the absorbent material for fluid contact with the delivery means whereby evaporable fluid is delivered to the absorbent material for evaporation.

5. The air freshener dispenser of claim 4 wherein the fixing member includes a pair of spaced annular flanges that position the absorbent material with the gripper member.

6. The air freshener dispenser of claim 4 wherein the absorbent material is configured to simulate a flower stamen.

7. An air freshener comprising:

a container having an opening and storing a fragrant evaporable liquid;

a head assembly connected to the container adjacent the opening and simulating the petals of a flower comprising a plurality of flexible cantilevered gripper members;

an absorbent material removably connected to the head assembly and operatively connected to the opening, the absorbent material extending upward from the container and configured to complement the simulated petals of the head assembly;

delivery means extending from the opening into the container to deliver the fragrant evaporable liquid to the absorbent material; and a fixing member, mounted between the gripper members and extending the absorbent material upward from the opening and the gripper members, having an upper top portion configured to simulate a pistil when removably connected to the head assembly and a lower annular flange for securing the absorbent material for fluid contact with the delivery means whereby evaporable liquid is delivered to the absorbent material for evaporation.

8. The air freshener dispenser of claim 7 wherein the absorbent material has a fringed edge configured to simulate a flower stamen.

9. The air freshener dispenser of claim 8 wherein the fixing members includes a pair of spaced annular flanges that position the absorbent material with the gripper members.

10. An air freshener dispenser comprising:

a container having an opening and storing a fragrant evaporable liquid;

a head assembly connected to the container adjacent the opening and simulating petals of a flower comprising a cylindrical member with an aperture coincident with the container opening and a plurality of bosses;

an absorbent material removably connected to the head assembly and operatively connected to the opening, the absorbent material extending upward from the container and configured to complement the simulated petals of the head assembly and spaced by the plurality of bosses from an upper surface of the cylindrical member;

delivery means extending from the opening into the container to deliver the fragrant evaporable liquid to the absorbent material; and a fixing member removably connected to the head assembly, mounted between the gripper members and extending the absorbent material upward from the opening and the gripper members, and securing the absorbent material for fluid contact with the delivery means whereby evaporable fluid is delivered to the absorbent material for evaporation.

11. The air freshener dispenser of claim 10 wherein the delivery means includes a wick member extending into the fragrant liquid and a wick holder member for mounting the wick member and extending over and into the container opening, the cylindrical member extending over the wick holder and securing it to the container.

12. An air freshener dispenser comprising:

a container having an opening and storing fragrant evaporable liquid;

a head assembly connected to the container adjacent the opening and simulating the petals of a flower comprising a cylindrical member with an aperture coincident with the container opening and a plurality of bosses;

an absorbent material removably connected to the head assembly and operatively connected to the opening, the absorbent material extending upward from the container and configured to complement the simulated petals of the head assembly and spaced from an upper surface of the cylindrical member by the plurality of bosses;

delivery means extending from the opening into the container to deliver the fragrant evaporable liquid to the absorbent material; and a fixing member having an upper top portion configured to simulate a pistil when removably connected to the head assembly and a lower annular flange for securing the absorbent material for fluid contact with the delivery means whereby evaporable liquid is delivered to the absorbent material for evaporation.

13. The air freshener of claim 12 wherein the delivery means includes a wick member extending into the fragrant liquid and a wick holder member for mounting the wick member and extending over and into the container opening, the cylindrical member extending over the wick holder and securing it to the container.

* * * * *